United States Patent
Pugliesi et al.

[11] Patent Number: 6,149,662
[45] Date of Patent: Nov. 21, 2000

[54] MEDICAL SCISSOR SHARPENER

[75] Inventors: Robert B. Pugliesi, Woodbury; Salvatore Cucinella, Lindenhurst, both of N.Y.

[73] Assignee: Miltex Technology Corporation, Wilmington, Del.

[21] Appl. No.: 09/149,843

[22] Filed: Sep. 8, 1998

Related U.S. Application Data

[60] Provisional application No. 60/058,391, Sep. 8, 1997.

[51] Int. Cl.$^7$ ........................................... A61B 17/32
[52] U.S. Cl. .............................. 606/174; 76/82.2; 451/45
[58] Field of Search .................... 606/174; D8/93, D8/91, 35, 63; 451/45; 76/82.2

[56] References Cited

U.S. PATENT DOCUMENTS

| | | | |
|---|---|---|---|
| D. 241,504 | 9/1976 | Krusche | D8/5 |
| D. 365,740 | 1/1996 | Smith | D8/93 |
| D. 375,241 | 11/1996 | Pigott | D8/93 |
| D. 404,278 | 1/1999 | Gore | D8/93 |
| D. 410,185 | 5/1999 | Huber | D8/93 |
| 4,508,314 | 4/1985 | Williams et al. | 76/82.2 |

FOREIGN PATENT DOCUMENTS

| | | |
|---|---|---|
| 621080A5 | 1/1981 | Switzerland . |
| 2163077A | 2/1986 | United Kingdom . |

*Primary Examiner*—Michael Buiz
*Assistant Examiner*—Anthony S. King
*Attorney, Agent, or Firm*—Levine & Mandelbaum

[57] ABSTRACT

A scissor sharpener has a recurved frame forming a U-shaped channel and an opening for receiving four fingers of a hand for grasping. A sharpening stone spans the channel at a predetermined angle to the adjacent surfaces of the frame. Surgical scissors can be wedged within the channel while their cutting edges are drawn over the stone for sharpening.

8 Claims, 2 Drawing Sheets

MEDICAL SCISSOR SHARPENER

This application claims benefit of provisional application Ser. No. 60/058,391, filed Sep. 8, 1997.

BACKGROUND OF THE INVENTION

This invention relates to the art of sharpening the working ends of scissors. More specifically, the invention is directed to enabling scissors to be sharpened on site where they are being used, e.g., in a surgical operating room, thereby avoiding down time or requiring a surgeon or other user of such scissors to work without a pair of scissors because they have become dull.

Hand-held medical scissors have traditionally been sharpened either by sending the scissors to an off-site repair facility or by using very costly electronic units that allow for sharpening of instruments on-site by a trained technician. When scissors are sent off-site for sharpening, it normally can take a week or longer before the sharpened scissors are returned and ready for use. Also, a fee must be paid for having the scissors sharpened each time they are sent out.

SUMMARY OF THE INVENTION

The present invention overcomes the above mentioned shortcomings by provided for a medical scissor sharpener comprising a frame having a perimeter with a recurved portion forming a U-shaped channel and an aperture spaced from said channel, to enable gripping of the frame, and a sharpening stone mounted in the frame and spanning the channel. The aperture has a major diameter large enough to enable four fingers of a human hand to be received in grooves along its inner circumference to enable gripping of the frame with a thumb of the hand in engagement with a dimple in the surface of the frame perimeter. The sharpening stone has a longitudinal axis projecting into the frame opening. Medical scissors and other types of scissors can be sharpened using the hand held scissor sharpening unit of the invention. Scissors are sharpened by swiping the blade of the instrument over a specifically angled ceramic stone. The sharpening unit itself can be sterilized, thereby making it suitable for use during surgical procedures without need for resterilization of an instrument that has been sharpened on it. The sharpening unit is designed so that anyone can pick up the unit and, in minutes, sharpen instruments like a professional.

It is, therefore, an object of the invention to provide a medical scissor sharpening tool that is easier to use than prior art scissor sharpeners.

Another object of the invention is to provide a medical scissor sharpening tool that can be operated while hand held.

Still another object of the invention is to provide a medical scissor sharpening tool that can be readily sterilized for use in a surgical environment.

A further object of the invention to provide a medical scissor sharpening tool that can be fabricated at relatively little cost.

DESCRIPTION OF THE PREFERRED EMBODIMENT

Figure 1:
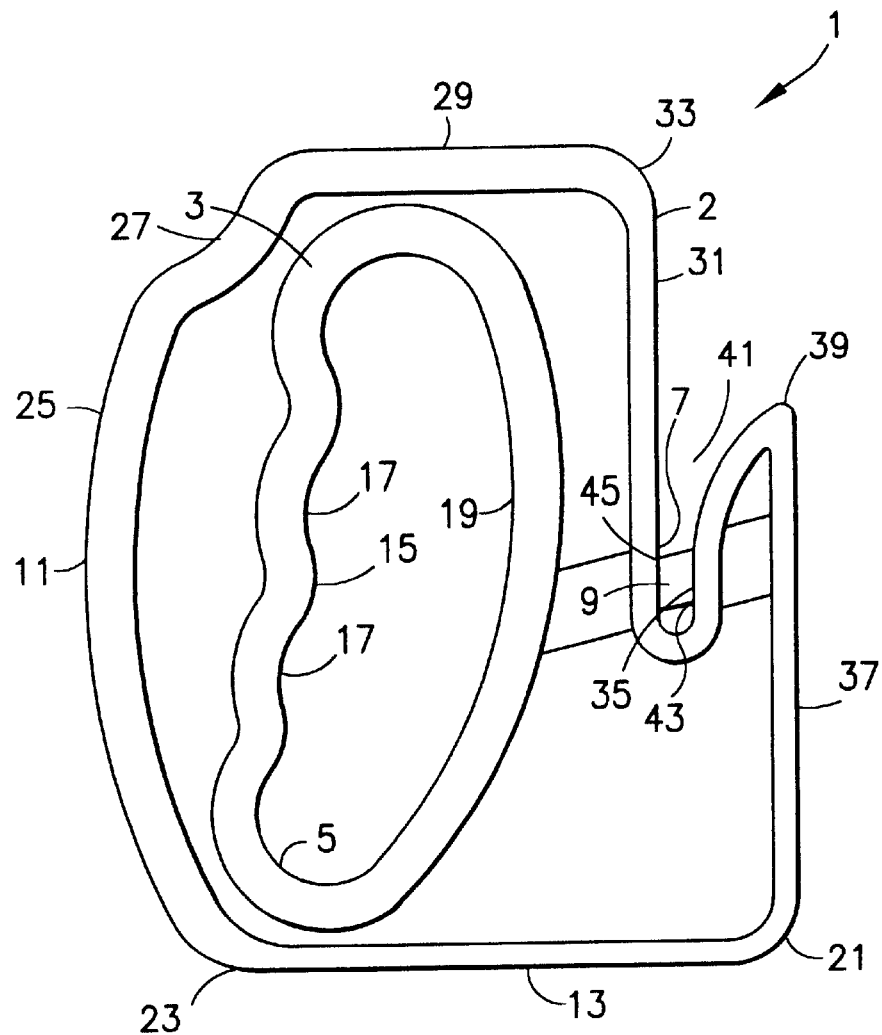
FIG. 1 is an elevation view of the preferred embodiment of the invention.

Referring to FIG. 1, there is shown a sharpening unit 1 in accordance with the invention. The sharpening unit 1 has a frame 2 with an integral handle 3 having an opening 5 for receiving the fingers of the hand which holds the sharpening unit. The frame 2 has a perimeter with a recurved portion forming a U-shaped channel 7 which serves as a guide as will be hereinafter explained.

The frame 2 is molded from a thermoplastic medical grade material, which in the preferred embodiment of the invention is an autoclavable plastic such as lexan. The frame is thicker along its outer perimeter, at the circumference of the opening 5, and where it surrounds the bores in which the sharpening stone is received, than it is elsewhere. In the preferred embodiment of the invention, the maximum thickness of the frame 2 is approximately ½ inch.

The opening 5 for receiving the fingers of the hand of the user has a major diameter of approximately 3¼ inches and a minor diameter measured from the ridge 15 between the two middle finger grooves 17 along the shortest distance to the opposite side 19 of the opening 5, of approximately 1 inch.

In the preferred embodiment of the invention, the frame 2 has a base 13 of approximately 3 inches in length from one end 21 to an opposite end 23. The right end 21 of the base 13 as seen in FIG. 1 turns upwardly 90 degrees at a rounded corner and extends to a height of approximately 2¹³⁄₁₆ inches. The left end 23 of the base turns upwardly into an outwardly curved profile 11 having a vertical height of approximately 3½ inches. The outer surface of the curved profile 11 then turns abruptly inward to a concave portion or dimple 27 which extends to a flat roof 29 of the frame 2 approximately 4¼ inches above and parallel to the base 13.

The flat roof 29 of the Frame has a length of approximately 2 inches running from the dimple 27 to where the roof 29 intersects a vertical exterior wall 31 of the frame 2 at a rounded corner 33. The wall 31 extends downwardly from the roof 29 for a length of approximately 2⅝ inches and then, at a re-curved portion of the outer surface of the frame, turns 180 degrees and runs upwardly to form a channel 7 which is approximately ¼ inch wide.

Coaxial cylindrical bores 43, 45 of like diameter are formed in the frame walls 31, 35 on opposite sides of the channel 7 for receiving the ends of the sharpening stone 9 which spans the channel 7. The sharpening stone in the preferred embodiment of the invention has a composition of aluminum oxide in an amount of 50%–90% by weight and other Oxides in an amount of 5%–50% by weight.

The cylindrical sharpening stone 9 has a longitudinal axis which, when extended, projects into the opening 5 in the frame 2 which is used to receive the fingers of the user's hand for grasping the sharpener 1. The sharpening stone 9 is mounted so that its axis forms an acute angle with the a major diameter of the grip opening 5 and the frame in the range of 60–75 degrees, and preferably of 67 degrees. The axis of the sharpening stone preferably makes an angle in the range of 75–80 degrees, and preferably 77 degrees, with a straight vertical outer frame wall 31 in which one end of the sharpening stone is received.

Figure 4:
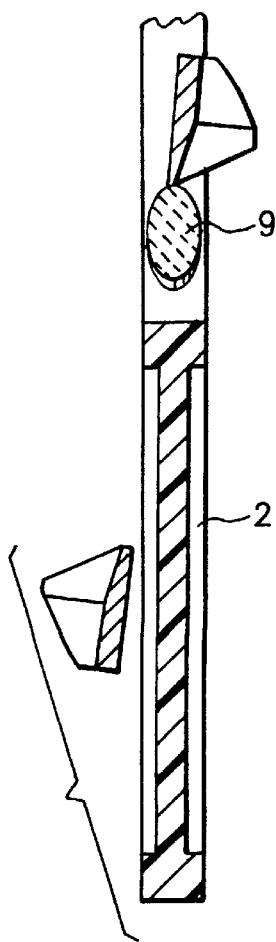
FIG. 4 is a sectional elevation view taken through line 4—4 of FIG. 3.

The upward running wall portion 35 of the channel 7 extends parallel to the opposite wall 31 for about half its length and then curves outwardly at a radius of 1 inch to meet a wall 37 of the frame extending from the base 13 at an apex 39 thereby forming a widened mouth 41 leading into the channel 7. The degree of curvature of the wall 35 is such that when a scissor is inserted into the channel 7 with its cutting edge at the intersection of the sharpening stone 9 and the straight wall 31, and the opposite dull edge of the scissor in engagement with the curved surface of the wall 35, the cutting edge of the scissor is in a plane tangential to the uppermost surface of the sharpening stone as best seen in FIG. 4.

Figure 2:
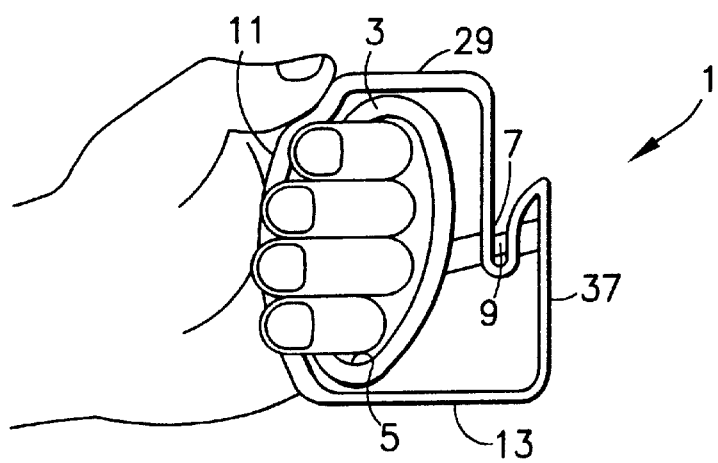
FIG. 2 is an environmental view illustrating a preferred way of holding the preferred embodiment of the invention.

In use the sharpening unit 1 of the invention is grasped in the left hand with its curved edge 11 resting firmly against the palm as shown in FIG. 2. For better control, the base 13 of the sharpening unit 1 can be held firmly against a flat surface, e.g., a table.

Figure 3:
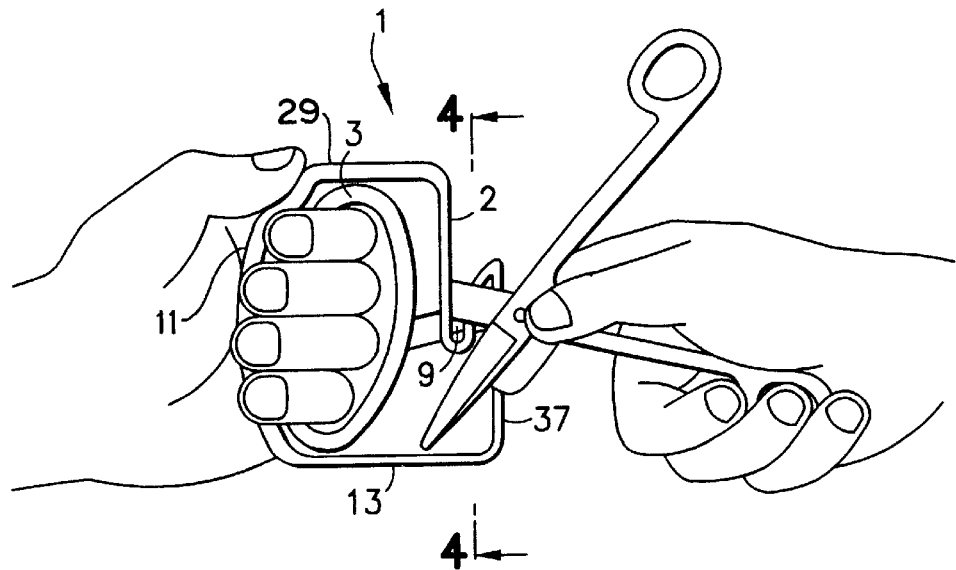
FIG. 3 is an environmental view illustrating the use of the preferred embodiment of the invention.

The scissors are grasped in the right hand at their screw joint and carefully held opened as shown in FIG. 3. The flat side of the inside blade of the scissors is placed against the sharpening unit 1 with its cutting edge resting on the sharpening stone 9 as shown in FIGS. 3 and 4. The blade of the scissor to be sharpened is then run through the sharpener by starting near the screw and pulling it along its entire length in one continuous motion. The foregoing motion is repeated until the blade is sharpened. The scissors are then turned over and the foregoing procedure is repeated to sharpen the opposite cutting edge.

It is to be appreciated that the foregoing is a description of a preferred embodiment of the invention to which variations and modifications may be made without departing from the spirit and scope of the invention.

What is claimed is:

1. A medical scissor sharpener comprising a frame having a perimeter with a recurved portion forming an open U-shaped channel bounded by a curved wall and an opposite wall, a portion of said curved wall curving upward and away from said opposite wall thereby forming a widened mouth leading into said open channel, and an aperture spaced from said channel, said aperture having a major diameter large enough to enable four fingers of a human hand to be received therein to enable gripping of the frame, and a sharpening stone mounted on said frame and having a longitudinal axis spanning said channel and projecting into said aperture at an acute angle relative to said aperture major diameter, the degree of curvature of said curved wall being such that when a scissor blade is inserted into said channel in engagement with said curved wall while its cutting edge is at the intersection of said sharpening stone and said opposite wall, the cutting edge of the scissor is in a plane tangential to a surface of said sharpening stone.

2. A medical scissor sharpener in accordance with claim 1 wherein a wall of the frame circumscribing the aperture has grooves for receiving fingers to aid in grasping.

3. A medical scissor sharpener in accordance with claim 2 wherein the frame has an outer circumferential wall with a dimple for receiving a thumb.

4. A medical scissor sharpener in accordance with claim 1 wherein said channel is bounded by a wall having an outer surface and said sharpening stone has an axis that intersects said wall surface at an angle in the range of 75–80 degrees.

5. A medical scissor sharpener in accordance with claim 4 wherein said sharpening stone axis intersects said wall surface at an angle of 77 degrees.

6. A medical scissor sharpener in accordance with claim 1 wherein said angle is in the range of 60–75 degrees.

7. A medical scissor sharpener in accordance with claim 6 wherein said angle is equal to 67 degrees.

8. A medical scissor sharpener in accordance with claim 1 wherein the sharpening stone comprises aluminum oxide in an amount of 50%–90% by weight and other oxides in an amount of 5%–50% by weight.

* * * * *